United States Patent [19]
Insley

[11] Patent Number: 4,650,479
[45] Date of Patent: Mar. 17, 1987

[54] SORBENT SHEET PRODUCT

[75] Inventor: Thomas I. Insley, Lake Elmo, Minn.

[73] Assignee: Minnesota Mining and Manufacturing Company, St. Paul, Minn.

[21] Appl. No.: 646,092

[22] Filed: Sep. 4, 1984

[51] Int. Cl.⁴ ............................................. A61F 13/16
[52] U.S. Cl. .................................. 604/358; 428/288; 428/221; 428/224; 428/369; 428/903; 428/913
[58] Field of Search ............... 428/221, 224, 288, 364, 428/369, 370, 297, 299, 400, 903, 913; 604/358, 367

[56] References Cited

U.S. PATENT DOCUMENTS

| | | | |
|---|---|---|---|
| 3,670,731 | 6/1972 | Harmon | 128/284 |
| 3,971,373 | 7/1976 | Braun | 128/146.2 |
| 4,011,067 | 3/1966 | Carey, Jr. | 55/354 |
| 4,100,324 | 7/1978 | Anderson | 428/288 |
| 4,118,531 | 10/1978 | Hauser | 428/224 |
| 4,235,237 | 11/1980 | Mesek et al. | 128/284 |
| 4,366,206 | 12/1982 | Tanaka | 428/373 |
| 4,374,175 | 2/1983 | Tanaka | 428/369 |
| 4,426,417 | 1/1984 | Meitner et al. | 428/195 |
| 4,429,001 | 1/1984 | Kolpin et al. | 428/283 |

FOREIGN PATENT DOCUMENTS

| | | |
|---|---|---|
| 0080382 | 1/1983 | European Pat. Off. |
| 2373274 | 7/1978 | France |
| 2006614 | 5/1979 | United Kingdom |
| 2061339 | 5/1981 | United Kingdom |
| 2098871 | 12/1982 | United Kingdom |

OTHER PUBLICATIONS

Wente, Van A., "Superfine Thermoplastic Fibers", in Industrial Engineering Chemistry, vol. 48, pp. 1342 et seq., (1956).
Report No. 4364 of the Naval Research Laboratories, published May 25, 1954, entitled "Manufacture of Superfine Organic Fibers" by Wente, Van A. et al.

Primary Examiner—James J. Bell
Attorney, Agent, or Firm—D. M. Sell; J. A. Smith; C. Truesdale

[57] ABSTRACT

A sorbent sheet product, particularly useful for disposal diapers, incontinent devices, and sanitary napkins, is provided. The sorbent sheet product comprises a coherent fibrous web that includes entangled blown polymeric fibers and high sorbency, liquid sorbent fibers intermingled with the blown polymeric fibers. The sorbent sheet product may also contain liquid transport fibers.

20 Claims, 1 Drawing Figure

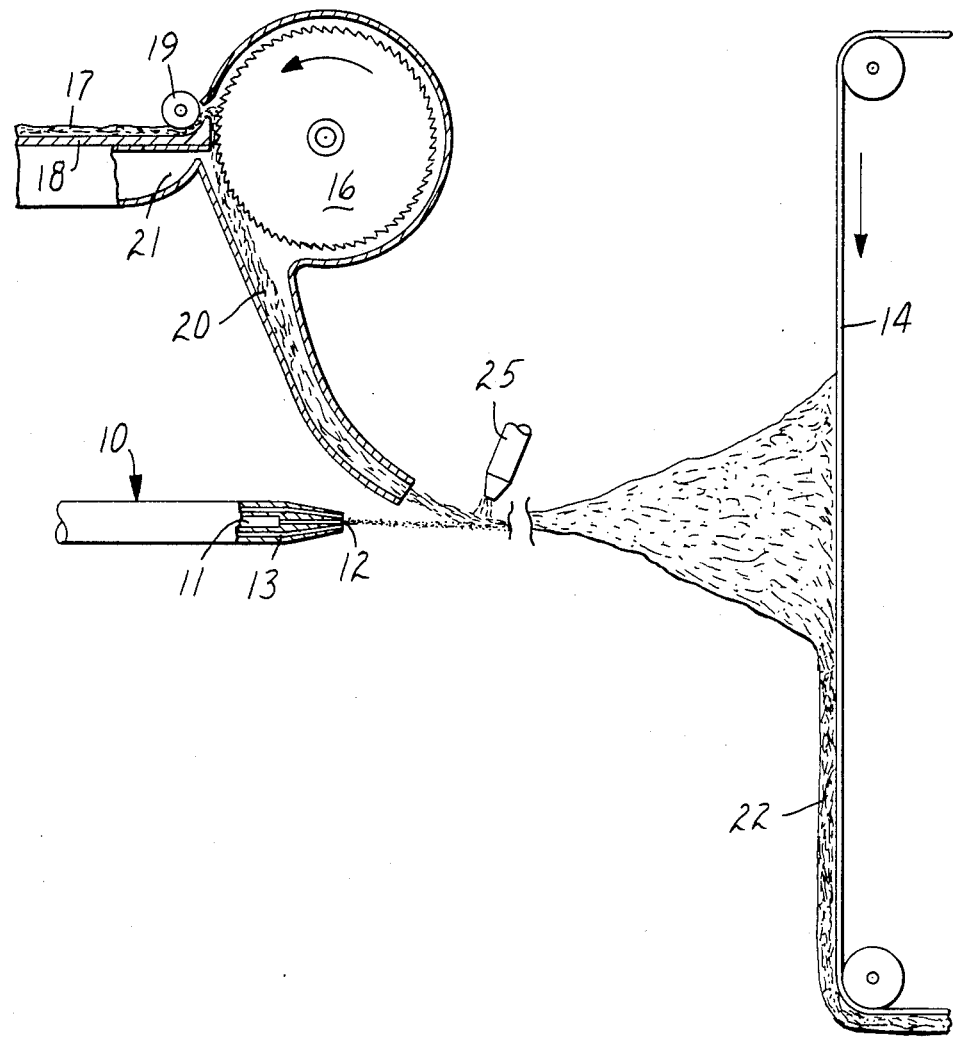

SORBENT SHEET PRODUCT

BACKGROUND OF THE INVENTION

1. Field of the Invention

The present invention relates to sorbent sheet products which provide rapid sorption and high liquid retention. Such products are useful in disposable incontinent devices, diapers, surgical swabs, bed pads, sanitary napkins, and wipers.

2. Description of the Prior Art

Sorbent sheet products having high fluid sorbency per unit weight and high fluid retention are desirable for sorption of fluids such as body exudates. It has been suggested that the sorbency of fibrous web product may be enhanced by the addition of various additives. U.S. Pat. No. 3,670,731 discloses the addition of hydrocolloidal particles to a fibrous mass, such as wood pulp, by cascading the particles into the fibrous mass. However, mechanical action causes the particles to dust out.

U.S. Pat. No. 4,235,237 discloses hydrocolloidal particles adhered to a fibrous web. This is achieved by contacting a fibrous web with hydrocolloidal sorbent particles dispersed in a volatile liquid, then vaporizing the liquid. Disadvantages of this approach include the need for multiple processing steps, limitations on the amount of particles that can be added to the web, brittleness of the dried web, and the tendency for particles to concentrate at the web surface.

U.S. Pat. No. 4,429,001 discloses the use of high sorbency particles in melt blown fiber webs. The melt blown fibers hold the particles to a large extent, but some dusting out of the particles may occur with mechanical action on the web. European Patent Application No. 0,080,382 also discloses sorbent particles in melt blown fiber webs. U.S. Pat. No. 4,426,417 discloses a nonwoven fiber matrix which includes melt blown fibers and a staple fiber mixture of synthetic and cotton fibers. However, this product sorbs only a limited amount of fluid and retention of fluid when the web is under pressure is low. British Patent Application No. 2,006,614 A discloses a melt blown fiber web treated with a wetting agent. This product also has disadvantages in that only a limited amount of fluid is absorbed and retention of fluid when the web is under pressure is limited.

SUMMARY OF THE INVENTION

The present invention provides a sorbent sheet product which exhibits no dusting out of sorbent material, has a soft, flexible hand, and has high liquid sorbency with excellent liquid retention. Briefly, this new sheet product comprises a coherent fibrous web that includes entangled blown fibers and high sorbency, liquid sorbent staple fibers intermingled with the blown fibers and uniformly dispersed and physically held within the web, the high-sorbency, liquid sorbent staple fibers swelling upon sorption of liquid. Additionally, the web may contain other constituents such as wetting agents and liquid conductive, liquid transport fibers.

The blown fibers may be prepared by extruding liquid fiber-forming material into a high-velocity gaseous stream, where the extruded material is attenuated and drawn into fibers. A stream of fibers is formed, which is collected, e.g., on a screen disposed in the stream, as an entangled coherent mass. According to the invention, high-sorbency, liquid sorbent staple fibers may be introduced into the stream of melt blown fibers, e.g., in the manner taught in U.S. Pat. No. 4,118,531, which is incorporated herein by reference, and the mixture of melt blown fibers and staple fibers is collected as an entangled coherent mass in which the high sorbency, liquid sorbent staple fibers are entrapped or otherwise physically held. The fibrous web containing the blown fibers and the high-sorbency, liquid sorbent staple fibers is formed in essentially one step, and the only further processing required may be simply cutting to size and packaging for use.

A sheet product of the invention is integral and handleable both before and after immersion in liquid, because the collected blown fibers are extensively tangled or snarled and form a strong coherent web, and the high-sorbency, liquid sorbent staple fibers are lastingly held and retained within this web.

Large quantities of liquid can be sorbed at a rapid rate, with the amount dependent principally on the sorption capacity of the sorbent staple fibers and the quantity of sorbent staple fibers contained within the web. Liquid is rapidly sorbed by portions of the sorbent staple fibers located in even the inner parts of the web, due to the sorbent staple fibers being held apart by the web structure and the portions of the sorbent staple fibers located at the exterior of the web conducting the liquid to portions of the sorbent staple fibers located in the interior portion of the web. The melt blown fibers of the web are preferably wet by the liquid being sorbed, e.g., as a result of use of a fiber-forming material that is wet by the liquid or by addition of a surfactant during the web-forming process, which further assists sorption.

The sorbent staple fibers swell and expand in size during sorption, and although the blown fibers are extensively entangled, the web of fibers expands as the sorbent staple fibers expand and the sorbed liquid tends to be retained in the product even when the product is subjected to pressure. The sorbent staple fibers also serve to separate the melt blown fibers, especially when in crimped form, producing a less dense web with greater potential for expansion on sorption of liquid. On sorption of liquid, the sorbent staple fibers allow the blown fibers to slip and move to a degree that the fibrous web is pushed apart by the swelling sorbent staple fibers while the web integrity is maintained.

The sorbent sheet product of the invention has a variety of uses, particularly where rapid sorption, high liquid retention, and soft hand are desired, such as in disposable incontinent devices, diapers, surgical swabs, bed pads, sanitary napkins, and filters for separating water from organic liquids.

BRIEF DESCRIPTION OF THE DRAWING

The drawing is a schematic diagram of apparatus used in practicing the present invention.

DETAILED DESCRIPTION

A representative apparatus useful for preparing sheet product of the invention is shown schematically in FIG. 1. The apparatus is generally similar to that taught in U.S. Pat. No. 4,118,531 for preparing a web of melt-blown fibers and crimped bulking fibers.

This apparatus prepares webs with melt-blown fibers (prepared by extruding molten fiber-forming material and which are preferred in many webs of the invention), but solution-blown and other types of fibers may also be used. The fiber-blowing portion of the illustrated apparatus can be a conventional structure as taught, for example, in Wente, Van A. "Superfine Thermoplastic Fibers", in Industrial Engineering Chemistry, Vol. 48, pages 1342 et seq (1956), or in Report No. 4364 of the Naval Research Laboratories, published May 25, 1954, entitled "Manufacture of Superfine Organic Fibers" by Wente, Van A.; Boone, C. D.; and Fluharty, E. L. Such a structure includes a die 10 which has an extrusion chamber 11 through which liquified fiber-forming material is advanced; die orifices 12 arranged in line across the forward end of the die and through which the fiber-forming material is extruded; and cooperating gas orifices 13 through which a gas, typically heated air, is forced at very high velocity. The high-velocity gaseous stream draws out and attenuates the extruded fiber-forming material, whereupon the fiber-forming material solidifies as fibers during travel to a collector 14. The collector 14 is typically a finely perforated screen, which in this case is in the form of a closed-loop belt, but which can take alternative forms, such as a flat screen or a drum or cylinder. Gas-withdrawal apparatus may be positioned behind the screen to assist in deposition of fibers and removal of gas. Alternatively, two dies may be used and arranged so that the streams of melt blown fibers issuing from them intersect to form one stream that continues to a collector 14.

The apparatus shown in FIG. 1 also includes means for introducing the sorbent staple fibers into the sheet product of the invention. The sorbent staple fibers are introduced into the stream of melt blown fibers through the use of a lickerin roll 16. A web 17 of sorbent staple fibers, typically a loose, nonwoven web such as prepared on a garnet machine or "Rando-Webber", is propelled along a table 18 under a drive roll 19 where the leading edge engages against the lickerin roll 16. The lickerin roll 16 turns in the direction of the arrow and picks the sorbent staple fibers from the leading edge of the web 17, dissociating the sorbent staple fibers from one another. The picked sorbent staple fibers are conveyed in an air stream to inclined duct 20 and into the stream of melt blown fibers where the sorbent staple fibers become mixed with the melt blown fibers. The air stream is generated inherently by rotation of the lickerin roll, or that air stream may be augmented by use of an auxilliary fan or blower operating through a duct 21 as is known in the art. The mixed stream of melt blown fibers and sorbent staple fibers then continues to the collector 14 where a web 22 of randomly intermixed and intertangled melt blown fibers and sorbent staple fibers is formed. A spray jet 25 may be used to apply materials, such as wetting agents, to the mixed stream of blown fibers and sorbent staple fibers prior to collection at collector 14.

Melt-blown fibers are greatly preferred for sheet products of the invention, but solution-blown fibers in which the fiber-forming material is made liquid by inclusion of a volatile solvent can also be used. U.S. Pat. No. 4,011,067 describes useful apparatus and procedures for preparing a web of such fibers; however, in preparing sheet products of this invention fiber-forming material is generally extruded through a plurality of adjacent orifices rather than the single orifice shown in the patent.

The sorbent staple fibers are preferably introduced into the fiber stream at a point where the blown fibers have solidified sufficiently that the blown fibers will form only a point contact with the sorbent staple fibers (as taught in U.S. Pat. No. 3,971,373). However, the sorbent staple fibers can be mixed with the melt blown fibers under conditions that will produce an area contact with the sorbent staple fibers.

Once the sorbent staple fibers have been intercepted in the blown fiber stream, the process for making the sheet product of the invention is generally the same as the process for making other blown fiber webs; and the collectors, methods of collecting, and methods of handling collected webs are generally the same as those for making known blown fiber webs.

The layer of melt blown fibers and sorbent staple fibers formed in any one revolution of the collection screen, and a completed sheet product of the invention may vary widely in thickness. For most uses of sheet products of the invention, a thickness between about 0.05 and 2 centimeters is used. For some applications, two or more separately formed sheet products of the invention may be assembled as one thicker sheet product. Also, sheet products of the invention may be prepared by depositing the stream of blown fibers and sorbent staple fibers onto another sheet material such as a porous nonwoven web which is to form part of the eventual sheet product. Other structures, such as impermeable films, can be laminated to a sheet product of the invention through mechanical engagement, heat bonding, or adhesives.

The blown fibers are preferably microfibers, averaging less than about 10 micrometers in diameter, since such fibers offer more points of contact with the sorbent staple fibers per unit volume of microfibers. Very small fibers, averaging less than 5 or even 1 micrometer in diameter, may be used. Solution-blown fibers have the advantage that they may be made in very fine diameters, including less than one micrometer. Larger fibers, e.g., averaging 25 micrometers or more in diameter, may also be prepared, especially by the melt-blowing process.

Blown fibrous webs are characterized by an extreme entanglement of the fibers, which provides coherency and strength to a web and also adapts the web to contain and retain the sorbent staple fibers. The aspect ratio (ratio of length to diameter) of blown fibers approaches infinity, though the fibers have been reported to be discontinuous. The fibers are long and entangled sufficiently that it is generally impossible to remove one complete fiber from the mass of fibers or to trace one fiber from beginning to end. Despite such entanglement, a sheet product will expand greatly in size during sorption.

The fibers may be formed from a wide variety of fiber-forming materials. Representative polymers for forming melt-blown fibers include polypropylene, polyethylene, polyethylene terephthalate, and polyamides. Representative polymers for forming solution-blown fibers include polymers or copolymers of vinyl acetate, vinyl chloride, and vinylidene chloride. Inorganic materials also form useful fibers. Fibers of different fiber-forming materials may be used in the same sheet product in some embodiments of the invention, either in mixture in one layer or in different layers.

Many of the fiber-forming materials form hydrophobic fibers, which can be undesirable in water sorbing sheet products. To improve the sheet product for such a use, a surfactant in powder or liquid form may be introduced into the sheet product, as by spraying liquids onto the web after it is formed. Useful surfactants, which typically comprise molecules having oleophilic and hydrophilic moieties, include dioctyl ester of sodium sulfosuccinate and alkylaryl polyether alcohol. A small amount of the surfactant, such as 0.05 to 1 weight percent of the sheet product, will generally provide adequate hydrophilicity, but larger amounts can be used. Use of oleophilic blown fibers together with water sorbent staple fibers can have the advantage of dual absorption, in that the blown fiber portion of the fibrous web sorbs organic liquids, such as oils, while the sorbent staple fibers sorb water.

As indicated above, the sorbent staple fibers used in the invention are super absorbent fibers, which rapidly absorb and retain under pressure large quantities of liquids. Tests useful in evaluating the sorbency of the super sorbent fibers and the sorbent sheet of the invention include the following:

Demand Sorbency Test

A 4.45 cm (1.75 inch) in diameter test sample of sorbent sheet or, in the case where sorbent fibers are to be tested, an air-laid web of sorbent fibers prepared by using, for example, a "Rando Webber", is placed on a 25–50μ porous plate in a filter funnel. A pressure of 1.0 kPa is applied to the sample by a plunger which is freely movable in the barrel of the funnel. Test fluid at zero hydrostatic head is conducted from a reservoir through a siphon mechanism to the upper surface of the porous plate where the test sample sorbs the test fluid. The amount of test fluid withdrawn from the reservoir by the test sample is then measured to determine the amount of test fluid sorbed by the test sample.

Centrifugal Retention Test

A 1 g sample of fiber or sheet product is placed in a centrifuge basket and the basket with sample is submerged in test solution for one hour. The basket with sample is removed, drained for 2–3 minutes, and placed in a centrifuge tube. The tube is placed in a centrifuge and subjected to a centrifugal force of 180 G for 10 minutes. The samples are removed and the amount of test solution retained is measured.

In the Demand Sorbency Tests and the Centrifugal Retention Tests where synthetic urine is used as the sorbed liquid, the synthetic urine has the following formulation:

| | |
|---|---|
| 0.06% | calcium chloride |
| 0.10% | magnesium sulfate |
| 0.83% | sodium chloride |
| 1.94% | urea |
| 97.07% | deionized water |

The synthetic urine solution has a conductance of 15.7 mΩ.

Fibers useful as sorbent staple fibers in the present invention are those having synthetic urine absorbency of at least 10 ml/g, preferably 30 ml/g, more preferably 70 ml/g, when tested according to the Demand Sorbency Test. The sorbent staple fibers preferably have a synthetic urine retention value of at least about 5 ml/g, more preferably at least 10 ml/g when tested according to the Centrifugal Retention Test.

To achieve high liquid sorbency and good liquid retention under pressure, the sorbent staple fiber should have at least one outside portion of highly hydrophilic material. Examples of such highly hydrophilic fibers are those prepared by treating acrylonitrile fibers with an alkali-metal hydroxide to form a hydrophilic crosslinked polymer on the surface thereof as disclosed in U.S. Pat. Nos. 4,366,206 and 4,374,175. Also useful are fibers having a sorbent coating such as a crosslinked, saponified copolymer of methacrylic acid and ethacrylic acid or a homopolymer of acrylic acid. A particularly useful fiber is "Lanseal F", an acrylonitrile fiber having a hydrophilic crosslinked polymer on the surface thereof, available from Japan Exlan Co., Ltd., Osaka, Japan.

The size of the sorbent staple fibers is preferably in the range of about 0.5 to 50 denier, more preferably about 1 to 30 denier, the fibers being slender elongated structures. The size of the sorbent staple fibers depends on the end use of the product with sorbent staple fibers of lower denier providing a softer hand. When using equipment such as a lickerin roll to dissociate the sorbent staple fibers during production of the product, the fibers should average between about 2 to 15 centimeters in length. Preferably, the sorbent staple fibers are less than about 7 to 10 centimeters in length.

The sorbent staple fibers may be crimped to further enhance the anti-blocking effect provided by the fibers. Crimped sorbent staple fibers provide additional freedom of expansion to the product as the sorbent particles swell during liquid sorption. Crimped sorbent staple fibers also provide bulk and resilience to the sorbent web, desirable characteristics for end uses such as disposable diapers and incontinent pads.

The amount of sorbent staple fibers included in the sheet product of the invention will depend on the particular use to be made of the product and the sorbency of the sorbent fibers. For most uses, at least 20 g/m$^2$ of sorbent staple fibers per 100 g/m$^2$ of blown fibers will be used to provide sufficient sorbency of the sorbed liquid to achieve the desired rapid sorbency. Generally, the amount of sorbent staple fiber will not exceed about 200 g/m$^2$ per 100 g/m$^2$ of the blown fibers to maintain the strength and integrity of the blown fiber matrix, though, greater weight amounts of sorbent fiber may be used when the denier of the fiber is higher. Preferably, the sheet product contains about 40 to 150 g/m$^2$ of sorbent fibers per 100 g/m$^2$ of the blown fiber.

To further enhance the sorbency of the sorbent sheet products of the invention, transport fibers which wick or transport the liquid being sorbed to inner portions of the sheet product may be included in the fibrous web. The transport fibers used in this preferred embodiment of the invention are generally absorbent staple fibers which rapidly absorb and wick the fluid being absorbed. Fibers useful as transport fibers are those having a water retention value of at least about 10%, preferably about 20% and more preferably about 25% when tested according to ASTM Test Method D2402 and a synthetic urine retention value of about at least 1 ml/g when tested according to the Centrifugal Retention Test. Fibers having such a water retention value have been found to provide a desired transport of liquid into the interior of the web. Such fibers include rayon, cotton, wool and silk. A particular preferred fiber is "Absorbit" rayon fiber supplied by American Enka Company.

The size of the transport fibers is preferably in the range of about 1 to 50 denier, more preferably about 1 to 30 denier. The size of the transport fibers depends on the end use of the product. Transport fibers of lower denier provide a softer hand. When using equipment such as a lickerin roll to dissociate the transport fibers during production of the product, the fibers should average between about 2 to 15 centimeters in length.

Preferably, the transport fibers are less than about 7 to 10 centimeters in length.

The transport fibers may be crimped to further enhance the anti-blocking effect provided by the fibers and to increase the resilience of the sorbent sheet product. Crimped staple transport fibers provide additional freedom of expansion to the product as the sorbent staple fibers swell during liquid sorption. This additional freedom of expansion reduces the tendency for the entangled blown fiber web to limit expansion of the web and thereby limit the quantity of water sorbed by the sorbent staple fibers. Crimped transport fibers provide a mechanical release of the web which reduces the constrictive forces on the swelling sorbent staple fibers during liquid sorption. However, the amount of crimp in the fiber cannot be so great as to excessively separate the blown fibers and sorbent staple fibers to the extent that the interstitial movement of fluid though the web is reduced.

The amount of transport fibers included in the sheet product of the invention will depend on the particular use to be made of the product and the amount and type of sorbent staple fibers included in the sheet product. Generally, at least 10 g/m$^2$ of transport fibers per 100 g/m$^2$ of blown fibers will be used to provide sufficient transport and wicking of the sorbed liquid to overcome any blocking effect resulting from the swollen sorbent fibers and to achieve the desired rapid sorbency. Generally, the amount of transport fiber will not exceed, about 100 g/m$^2$ per 100 g/m$^2$ of the blown fibers to maintain the strength and integrity of the blown fiber matrix, though greater weight amounts of transport fiber may be used when the denier of the fiber is higher. Preferably, the sheet product contains about 20 to 60 g/m$^2$ of transport fibers per 100 g/m$^2$ of the blown fiber.

The advantages of the sorbent sheet product of the invention are illustrated in the following examples which are not to be construed as limiting its scope.

EXAMPLES 1–5 AND COMPARATIVE EXAMPLE 1

In Examples 1–5, sorbent sheet products were prepared from polypropylene microfibers and sorbent staple fibers using the apparatus shown in the drawing. The sorbent staple fibers used were "Lanseal F" fibers, 7 denier, 51 mm in length, available from Japan Exlan Co., Ltd., Osaka, Japan. In each Example, the sorbent sheet contained 100 g/m$^2$ of the polypropylene microfibers, sorbent staple fibers in the amounts indicated in Table 1 and 0.4 g/m$^2$ of "Triton GR-5", a cationic surfactant available from Rohm and Haas Company. Comparative Example 1 was prepared from polypropylene microfibers without the addition of sorbent staple fibers. Demand sorbency tests were then conducted on each prepared sheet using deionized water. The results are shown in Table 1.

TABLE 1

|  | Amount of Microfiber (g/m$^2$) | Amount of Sorbent Fiber (g/m$^2$) | Weight of Liquid Sorbed for Time Shown (l/m$^2$) | | | | | |
| --- | --- | --- | --- | --- | --- | --- | --- | --- |
|  |  |  | 1 min | 2 min | 3 min | 4 min | 5 min | 6 min |
| Example 1 | 100 | 20 | 1.8 | 3.1 | 4.0 | 4.5 | 4.8 | 4.9 |
| Example 2 | 100 | 40 | 1.9 | 3.4 | 4.4 | 5.2 | 5.6 | 5.7 |
| Example 3 | 100 | 60 | 1.2 | 2.3 | 3.4 | 4.3 | 5.2 | 6.0 |
| Example 4 | 100 | 100 | — | 1.7 | — | 3.1 | — | 4.3 |
| Example 5 | 100 | 150 | — | 1.3 | — | 2.0 | — | 2.6 |
| Comparative Example 1 | 100 | 0 | 1.2 | 1.3 | 1.3 | 1.3 | 1.3 | 1.3 |

As can be seen from the data in Table 1, the most rapid sorption of water was achieved by the sheet products of Examples 2 and 3. The sheet products of Examples 4 and 5 did not sorb the water as rapidly as those of Examples 2 and 3 due to gel blocking, a condition where the sorbent fibers with sorbed liquid on the outer portion of the sheet form a gel which then acts as a dam inhibiting liquid from passing to the inner portions of the sheet.

EXAMPLES 6–10 AND COMPARATIVE EXAMPLES 2 AND 3

In Examples 6–10, sorbent sheet products were prepared as in Examples 1–5 with polypropylene microfibers, sorbent staple fibers and surfactant. Comparative Example 2 was prepared from polypropylene microfibers without the addition of sorbent staple fibers. Comparative Example 3 was prepared from air-laid sorbent staple fiber without the addition of microfibers using a "Rando-Webber". Demand sorbency tests were then conducted on each prepared sheet using synthetic urine. The results are shown in Table 2. Centrifugal retention tests were also conducted on the sheets of Examples 6–10 and Comparative Example 3 using synthetic urine. The results are shown in Table 3.

TABLE 2

|  | Amount of Microfiber (g/m$^2$) | Amount of Sorbent Fiber (g/m$^2$) | Weight of Liquid Sorbed for Time Shown (l/m$^2$) | | | |
| --- | --- | --- | --- | --- | --- | --- |
|  |  |  | 0.5 min | 1.0 min | 1.5 min | 2.0 min |
| Example 6 | 100 | 20 | 1.8 | 2.6 | 2.8 | 2.7 |
| Example 7 | 100 | 40 | 1.7 | 2.6 | 2.8 | 2.8 |
| Example 8 | 100 | 60 | 1.6 | 2.8 | 3.5 | 3.5 |
| Example 9 | 100 | 100 | 1.1 | 2.1 | 3.0 | 3.8 |
| Example 10 | 100 | 150 | 0.7 | 1.5 | 2.4 | 3.2 |
| Comparative Example 2 | 100 | 0 | 1.2 | 1.3 | 1.3 | 1.3 |
| Comparative Example 3 | 0 | 100 | 0.3 | 0.9 | 1.4 | 1.9 |

TABLE 3

|  | Retention (ml/g) |
| --- | --- |
| Example 6 | 3.0 |

TABLE 3-continued

| | Retention (ml/g) |
|---|---|
| Example 7 | 3.7 |
| Example 8 | 4.4 |
| Example 9 | 5.6 |
| Example 10 | 8.1 |
| Comparative Example 3 | 13.4 |

As can be seen from the data in Table 2, the most rapid sorption of synthetic urine was achieved by the sheet products of Examples 8 and 9 after 2 minutes of testing. Examples 6 and 7 sorbed less synthetic urine due to lower loading of the super sorbent fiber. Example 10 showed less sorption due to gel blocking. Comparative Example 2, containing only blown microfibers, exhibited low sorption, while Comparative Example 3, containing only super sorbent fiber, showed low sorption during the 2 minute test period due to gel blocking.

EXAMPLE 11

A sorbent sheet product was prepared from polypropylene microfibers, sorbent staple fibers and rayon transport fibers. The sorbent staple fibers used were "Lanseal F" fibers, 7 denier, 51 cm in length and the rayon transport fibers used were "Absorbit" fibers supplied by American Enka Company. The sorbent sheet product was prepared using the apparatus shown in the drawing with both the sorbent staple fibers and the transport fibers being fed by the lickerin roll. The composition of the sorbent sheet product was b 100 g/m$^2$ polypropylene microfiber, 50 g/m$^2$ sorbent staple fiber, 50 g/m$^2$ rayon transport fiber, and 0.4 g/m$^2$ cationic surfactant. Demand sorbency tests were then conducted on the sorbent sheet using synthetic urine. The results are shown in Table 4.

TABLE 4

| Time (min) | Weight of Liquid Sorbed (l/m$^2$) |
|---|---|
| 0.5 | 1.7 |
| 1.0 | 2.9 |
| 1.5 | 3.6 |
| 2.0 | 4.0 |
| 2.5 | 4.1 |

As shown by the data in Table 4, the rate of sorption of a sorbent sheet product can be enhanced by adding transport fibers to the sheet to wick the synthetic urine test solution into the sheet. The rate of sorbency of the sheet product of Example 11 is superior to any of Examples 6–10 due to the wicking action of the transport fibers.

What is claimed is:

1. A sorbent sheet product comprising a nondusting, coherent fibrous web that includes entangled blown polymeric fibers and high sorbency, liquid-sorbent fibers intermingled with the blown polymeric fibers, said high sorbency fibers having a synthetic urine retention value of at least about 5 ml/g.

2. The sorbent sheet product of claim 1 wherein the high sorbency, liquid-sorbent fibers are present in an amount of about 20 to 200 g/m$^2$ for 100 g/m$^2$ of blown polymeric fibers.

3. The sorbent sheet product of claim 1 wherein the blown polymeric fibers are microfibers having an average diameter less than about 10 micrometers.

4. The sorbent sheet product of claim 1 wherein said blown fibers are selected from polypropylene, polyethylene, polyethylene terephthalate, and polyamide fibers.

5. The sorbent sheet product of claim 1 wherein the high sorbency, liquid sorbent fibers are acrylonitrile fibers having at least a portion of the surface modified to form a hydrophilic crosslinked polymer thereon.

6. The sorbent sheet product of claim 1 further comprising surfactant.

7. The sorbent sheet product of claim 6 wherein the surfactant is present in an amount of 0.1 to 1.0 g/m$^2$ for 100 g/m$^2$ of blown polymeric fibers.

8. The sorbent sheet product of claim 1 further comprising transport fibers having a synthetic urine retention value of at least 1.0 ml/g.

9. The sorbent sheet product of claim 8 wherein said transport fibers are selected from rayon, cotton, wool, and silk.

10. The sorbent sheet product of claim 8 wherein said transport fibers are rayon.

11. The sorbent sheet product of claim 8 wherein said transport fibers are present in an amount of about 10 to 100 g/m$^2$ for 100 g/m$^2$ blown polymeric fibers.

12. The sorbent sheet product of claim 8 wherein said transport fibers are crimped.

13. A disposable diaper containing the sorbent sheet product of claim 1.

14. A disposable incontinent device containing the sorbent sheet product of claim 1.

15. A sanitary napkin containing the sorbent sheet product of claim 1.

16. A sorbent sheet product comprising a nondusting, coherent fibrous web that includes entangled blown polymeric fibers and high sorbency, liquid-sorbent, staple fibers and transport fibers intermingled with the blown polymeric fibers, said high sorbency fibers having a synthetic urine retention value of at least about 5 ml/g, said transport fibers having a synthetic urine retention value of at least 1 ml/g, and said blown polymeric fibers having an average diameter less than about 10 micrometers.

17. The sorbent sheet product of claim 16 wherein the high sorbency, liquid-sorbent staple fibers are acrylonitrile fibers having at least a portion of the surface modified to form a hydrophilic crosslinked polymer thereon.

18. The sorbent sheet product of claim 16 further comprising surfactant.

19. The sorbent sheet product of claim 16 or 17 wherein the transport fibers are rayon.

20. The sorbent sheet product of claim 1 wherein said high absorbency, liquid-sorbent fibers are 0.5 to 50 denier and 2 to 15 centimeters in length.

* * * * *

UNITED STATES PATENT AND TRADEMARK OFFICE
CERTIFICATE OF CORRECTION

PATENT NO.   :  4,650,479

DATED        :  MARCH 17, 1987

INVENTOR(S)  :  THOMAS I. INSLEY

It is certified that error appears in the above-identified patent and that said Letters Patent is hereby corrected as shown below:

Col. 9, line 26, delete "cm" and insert -- mm -- .

Signed and Sealed this

Third Day of April, 1990

Attest:

HARRY F. MANBECK, JR.

Attesting Officer

Commissioner of Patents and Trademarks